United States Patent
Winston et al.

[11] Patent Number: 5,858,333
[45] Date of Patent: Jan. 12, 1999

[54] TWO-PART ORAL PRODUCTS AND METHODS OF USING SAME TO REMINERALIZE TEETH

[75] Inventors: Anthony E. Winston, East Brunswick; Norman Usen, Marlboro, both of N.J.

[73] Assignee: Enamelon, Inc., Cranbury, NJ

[21] Appl. No.: 131,314

[22] Filed: Aug. 7, 1998

[51] Int. Cl.⁶ .............................. A61K 7/16; A61K 7/18; A61K 9/65
[52] U.S. Cl. .............................. 424/57; 424/48; 424/49; 424/52; 424/435; 424/440; 106/35
[58] Field of Search .......................................... 424/49–88

[56] References Cited

U.S. PATENT DOCUMENTS

| | | | |
|---|---|---|---|
| Re. 33,161 | 2/1990 | Brown et al. | 423/308 |
| 4,080,440 | 3/1978 | Diguilio et al. | 424/49 |
| 4,083,955 | 4/1978 | Grabenstetter et al. | 424/49 |
| 4,397,837 | 8/1983 | Raaf et al. | 424/51 |
| 4,556,651 | 12/1985 | Brown et al. | 424/151 |
| 4,612,053 | 9/1986 | Brown et al. | 106/35 |
| 5,037,639 | 8/1991 | Tung | 424/57 |
| 5,145,668 | 9/1992 | Chow et al. | 424/52 |
| 5,268,167 | 12/1993 | Tung | 424/52 |
| 5,427,768 | 6/1995 | Tung | 424/52 |
| 5,437,857 | 8/1995 | Tung | 424/52 |
| 5,460,803 | 10/1995 | Tung | 424/57 |
| 5,476,647 | 12/1995 | Chow et al. | 424/52 |
| 5,522,893 | 6/1996 | Chow et al. | 623/11 |
| 5,525,148 | 6/1996 | Chow et al. | 106/35 |
| 5,534,244 | 7/1996 | Tung | 424/52 |
| 5,542,973 | 8/1996 | Chow et al. | 106/35 |
| 5,545,254 | 8/1996 | Chow et al. | 106/35 |
| 5,562,895 | 10/1996 | Tung | 424/57 |
| 5,571,502 | 11/1996 | Winston et al. | 424/52 |
| 5,603,922 | 2/1997 | Winston et al. | 424/49 |
| 5,605,675 | 2/1997 | Usen et al. | 424/49 |
| 5,614,175 | 3/1997 | Winston et al. | 424/52 |
| 5,645,853 | 7/1997 | Winston et al. | 424/440 |
| 5,695,729 | 12/1997 | Chow et al. | 423/305 |

*Primary Examiner*—Shep K. Rose
*Attorney, Agent, or Firm*—Depaoli & Frenkel, P.C.

[57] ABSTRACT

A two-part oral product capable of remineralizing subsurface lesions and/or mineralizing exposed dentinal tubules in teeth is composed of cationic and anionic discrete parts. The cationic discrete part contains at least one water-soluble calcium salt and, preferably, at least one non-toxic, water-soluble salt of a divalent metal other than calcium, and a first pharmaceutically acceptable carrier. The anionic discrete part contains at least one water-soluble phosphate salt and, preferably, at least one water-soluble fluoride salt, and a second pharmaceutically carrier. Preferably, one of the carriers is an aqueous carrier and the other of the carriers is a non-aqueous carrier. The cationic and anionic parts are simultaneously released from the product upon mixing of the product with water and/or saliva to form the mixed aqueous solution. In this way, calcium ions released by the calcium salt and phosphate ions released by the phosphate salt are simultaneously delivered to the tooth surfaces by the solution. To effect subsurface remineralization and/or mineralization, the parts are mixed together to form the mixed aqueous solution, and the solution is then promptly applied to the teeth for a period of time sufficient to allow calcium ions and phosphate ions to diffuse through the tooth surface to the subsurface, where the ions react to form an insoluble precipitate onto the lesion and/or tubule, thereby remineralizing such lesion and/or mineralizing such tubule.

21 Claims, No Drawings

TWO-PART ORAL PRODUCTS AND METHODS OF USING SAME TO REMINERALIZE TEETH

BACKGROUND OF THE INVENTION

This invention relates to oral products and methods of using same. More particularly, this invention relates to two-part oral products and methods of using same to remineralize subsurface lesions in teeth, mineralize exposed dentinal tubules, and prevent demineralization of the teeth.

Dental caries, i.e., tooth decay, is a leading cause of tooth damage in humans. Dental caries begins with lesions of so-called "white spots", which are demineralized areas below the surface of intact dental enamel. Subsurface lesions are formed before a cavity is detectable. If unchecked, surface enamel above a subsurface lesion eventually collapses, leading to cavitation and subsequent loss of tooth structure.

The primary component of the enamel and dentin in teeth is calcium phosphate in the form of calcium hydroxyapatite. Calcium hydroxyapatite is highly insoluble at normal oral pHs but relatively soluble in acidic media. Thus, carious lesions can form in the teeth when the teeth are exposed to acids, such as, e.g., those acids produced during the glycolysis of sugars by the action of various oral bacteria.

Saliva is supersaturated with respect to calcium and phosphate ions. Consequently, saliva can help protect the teeth against demineralization and can slowly remineralize teeth which have become demineralized. The presence of fluoride ions in the oral cavity can enhance the natural remineralization process, this being one of the accepted mechanisms by which fluoride toothpastes and mouthrinses protect against caries.

However, the efficacy of fluoride-containing toothpastes and mouthrinses to remineralize teeth is limited by the modest levels of calcium and phosphate in saliva.

Thus, it is highly desirable to increase the available concentration of calcium and phosphate ions in the oral cavity to speed up the remineralization process. However, because of calcium phosphate's low solubility at the pH of saliva, the addition of higher levels of dissolved calcium and phosphate ions is not easily accomplished.

Remineralization of dental enamel has been carried out experimentally, both in vivo and in vitro. Some studies have concentrated on the remineralizing properties of saliva and of synthetic solutions supersaturated with respect to hydroxyapatite. Such studies comprise the subject matter of U.S. Pat. Nos. 3,679,360 (Rubin) and 4,097,935 (Jarcho).

Generally, the supersaturated solutions or slurries used in the aforementioned Rubin and Jarcho patents for remineralization experiments have been prepared from a single form of calcium phosphate. When a carious lesion is flooded with one of these supersaturated solutions, the calcium and phosphate ions in the form of precipitated hydroxyapatite remineralize the lesion. However, use of these solutions is impractical for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because such solutions cannot maintain their supersaturated state. When the hydroxyapatite precipitates out to the point where the solution is no longer supersaturated, new supersaturated solution must be introduced or the remineralization process stops.

Thus, there is a need for a method of remineralizing dental enamel that does not require excessive amounts of solution or inordinately long or frequent exposure times.

Another problem with single calcium phosphate slurries is that as the hydroxyapatite precipitates out of solution, the pH of the solution changes. Unless the old solution is removed from contact with the tooth material, the solution may become too acidic or alkaline and may damage the dental tissue.

U.S. Pat. No. 4,080,440 (Digiulio et al) discloses a metastable solution of calcium and phosphate ions at a low pH (between 2.5 and 4.0) under which conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et al) disclose a remineralizing solution containing supersaturated concentrations of calcium ions, phosphate ions and a fluoride source stabilized by the presence of an antinucleating agent such as diamine tetramethylenephosphonic acid, ethylenediamine tetramethylenephosphonic acid and 2-phosphonobutane-tricarboxylic acid-1,2,4, or the water-soluble salts thereof. This solution is preferably adjusted to the neutral pH range where the solution is alleged to most effectively remineralize subsurface lesions. Even though the antinucleating agent would be expected to stabilize the solution, equilibrium of the supersaturated concentrations is still found difficult to maintain and avoid precipitation of hydroxyapatite and changes in the pH of the solution.

U.S. Pat. Nos. 4,083,955 (Grabenstetter et al) and 4,397,837 (Raaf et al) disclose a process for remineralizing demineralized enamel by the consecutive treatment of tooth surfaces with separate solutions containing calcium ions and phosphate ions. In this process, fluoride ions may be present in the phosphate solutions. It is immaterial which ionic solution is used to treat the teeth first. By sequentially applying calcium and phosphate ions to the tooth surface, high concentrations of the ions are able to penetrate into lesions in solution form, where the ions precipitate as a calcium phosphate salt when ions from the second treatment solution diffuse in. While apparently successful, this method involves the inconvenience of a plurality of sequential applications, which can also be time consuming.

U.S. Patent No. 4,606,912 (Rudy et al.) teaches a method of making a clear aqueous mouthwash solution capable of remineralizing lesions in teeth by forming an aqueous solution containing a source of calcium ions and a chelating agent for calcium ions, causing the chelation of at least 50% of the calcium ions and subsequently adding a source of phosphate ions to the aqueous solution. Here too, while somewhat effective, the addition and necessary control of the amount of chelating agent makes the concept impractical.

Another problem with known remineralization techniques is that the remineralization may stop before the lesion is completely remineralized due to build-up of the remineralized tooth material in or on the outer layer of the tooth's surface. This build-up occurs when the rate of remineralization is too fast and prevents the diffusion of the mineral into the deeper regions of the lesion, thus thwarting the full remineralization of the tooth.

U.S. Pat. Nos. 5,037,639; 5,268,167; 5,437,857; 5,427,768; and 5,460,803 (all to Tung) involve the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite).

In the methods taught in the Tung patents, remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

The Tung patents also teach the use of two-part solutions wherein a first part contains phosphate salt(s) and a second part contains calcium salt(s), wherein either the first part or the second part further contains carbonate salt(s). In addition, the Tung patents teach solutions formed by dissolving in water a solid powder containing calcium salt(s), phosphate salt(s), and carbonate salt(s). These solutions are than applied to dental tissue. The Tung patents further teach the use of non-carbonated solid powders containing mixtures of calcium salts and phosphate salts which can be applied directly to the tooth or dispersed in gel, chewing gum, or other non-aqueous mediums such as toothpaste which is placed in contact with the tooth. The patents to Tung teach that these powders are easily dissolved in saliva and then reprecipitated as an amorphous calcium phosphate compound. However, the Tung patents do not disclose the pHs of aqueous solutions formed from the non-carbonated solid powder.

Effective remineralizing products and methods are continually desired which do not require the presence of carbonate salts to achieve stability, remineralization and/or mineralization. It is also continually desirable to provide remineralizing products and methods which directly form hydroxyapatite at the subsurface of the tooth rather than first forming an amorphous calcium phosphate as an intermediate.

Remineralizing products which overcome many of the aforementioned problems are disclosed in U.S. Patent Nos. 5,603,922 (Winston et al.); 5,605,675 (Usen et al.); 5,571,502 (Winston et al.); 5,614,175 (Winston et al.); and 5,645,853 (Winston et al.). Reference is also made to copending, commonly assigned U.S. patent application Ser. Nos. 08/669,724 (filed Jun. 26, 1996); 08/722,459 (filed Sep. 27, 1996); 08/670,897 (filed Jun. 26, 1996); 08/722,457 (filed Sept. 27, 1996); 08/691,328 (filed Aug. 2, 1996); and 08/832,827 (filed Apr. 3, 1997).

U.S. Pat. No. 5,603,922 (Winston et al.) discloses one-part and two-part products and methods of using same to remineralize subsurface lesions, wherein the products contain at least one water-soluble calcium salt, at least one water-soluble salt of a divalent metal other than calcium and at least one water-soluble phosphate salt. In the two-part products, the calcium and divalent metal salts are disposed in a first discrete component, and the phosphate salt(s) is disposed in a second discrete component. The two-part product may further contain a dispensing means for simultaneously dispensing the first and second components from the product so as to permit the dispensed first and second components to simultaneously contact the tooth or teeth being treated.

U.S. Patent No. 5,605,675 (Usen et al.) discloses a two-part product and method of using same for remineralizing dental enamel, wherein the product contains a first discrete component containing at least one water-soluble calcium salt and a second discrete component containing at least one water-soluble phosphate salt and at least one water-soluble fluoride salt. The product may further contain a means for simultaneously dispensing the first and second components from the product.

U.S. Pat. No. 5,645,853 (Winston et al.) discloses a chewing gum product and method of using same to remineralize subsurface lesions in teeth, wherein the product contains a water-soluble cationic portion composed of at least one water-soluble calcium salt and at least one water-soluble, non-toxic salt of a divalent metal other than calcium; a water-soluble anionic portion containing at least one water-soluble phosphate salt; and a gum base. The anionic and cationic portions are disposed in the product such that chewing of the product in the presence of water and/or saliva causes the anionic and cationic portions to be simultaneously released into the water and/or saliva so as to form a mixed aqueous solution therewith.

U.S. Pat. Nos. 5,571,502 and 5,614,175 (both to Winston et al.) each disclose one-part, non-aqueous products and methods of using same for remineralizing subsurface lesions, wherein the products contain at least one water-soluble calcium salt; at least one water-soluble phosphate salt; either a stabilizer or a hydrophilic, non-aqueous, water-soluble vehicle; and, optionally, at least one water-soluble fluoride salt. In the two-part products disclosed in the foregoing patents, separation of the cationic and anionic components is generally achieved by disposing the components in separate compartments of a two-compartment container. Although separation in this way is effective in preventing premature reaction of the cationic and anionic components, it is continually desirable to provide other ways to achieve separation of these components.

A primary object of this invention is to provide a two-part oral product capable of remineralizing subsurface lesions in teeth, mineralizing exposed dentinal tubules, and preventing demineralization of the teeth.

A further object of this invention is to provide a remineralizing, two-part oral product containing a discrete calcium part and a discrete phosphate part, wherein the calcium and phosphate parts are separated from one another by means other than a physical barrier therebetween.

Another object of this invention is to provide a remineralizing, two-part oral product the use of which does not require excessive amounts of solution or inordinately long or frequent exposure times.

Still another object of the present invention is to provide a remineralizing, two-part oral product which is easily usable by the consumer and does not differ significantly, in flavor or appearance, from customary dental cosmetics.

A further object of the present invention is to provide a method of remineralizing subsurface lesions, mineralizing exposed dentinal tubules and preventing demineralization of teeth, using a two-part oral product having the aforementioned characteristics.

These and other objects which are achieved according to the present invention can be readily discerned from the following description.

SUMMARY OF THE INVENTION

The present invention achieves subsurface remineralization by means of an oral product containing discrete cationic and anionic parts which are kept separate from one another until the product is ready for use. The cationic part contains at least one water-soluble calcium salt capable of releasing calcium ions and the anionic part contains at least one water-soluble phosphate salt capable of releasing phosphate ions and, preferably, at least one water-soluble fluoride salt capable of releasing fluoride ions.

While applicants do not wish the scope of the present invention to be limited by theory, it is believed that the calcium, phosphate and, if present, fluoride, ions diffuse through the tooth surface to the demineralized subsurface and precipitate in the demineralized subsurface. This is surprising because sufficient calcium, phosphate and, if present, fluoride, ions remain soluble for a period of time sufficient to permit their diffusion into the demineralized subsurface of the dental enamel. This is accomplished by combining the particular ions just prior to their application to the tooth in a solution having a pH of from about 4.5 to about 10.0, preferably a pH of from about 5.0 to about 7.0, at which pH enough of the calcium, phosphate and fluoride ions remain soluble for a period of time required to remineralize the subsurface lesions and/or exposed dentinal tubules. In the present invention, the calcium and phosphate salts are stored separately to avoid premature precipitation of calcium phosphate.

Accordingly, one aspect of the present invention is directed to a two-part oral product for remineralizing at least one subsurface lesion in a tooth and/or mineralizing at least one exposed dentinal tubule of a tooth, wherein the product contains:

(A) a discrete cationic part containing an effective amount of at least one water-soluble calcium salt and, preferably, an effective amount of at least one salt of a divalent metal other than calcium, the calcium salt and the divalent metal salt being disposed in a first pharmaceutically acceptable carrier; and (B) a discrete anionic part containing an effective amount of at least one water-soluble phosphate salt and, preferably an effective amount of at least one water-soluble fluoride salt, the phosphate salt and the fluoride salt being disposed in a second pharmaceutically acceptable carrier;

wherein one of the first and second pharmaceutically acceptable carriers is an aqueous carrier and the other of the carriers is a non-aqueous, hydrophilic carrier.

The cationic and anionic parts are capable of being simultaneously released from the product of this invention when the product is mixed with water and/or saliva to form a mixed aqueous solution. Such mixed aqueous solution contains calcium ions released by the calcium salt and phosphate ions released by the phosphate salt. The solution delivers the calcium and phosphate ions to the tooth surface such that the calcium and phosphate ions simultaneously contact the tooth surface and remineralizing concentrations of the calcium and phosphate ions simultaneously diffuse through the tooth surface to the subsurface so as to effect subsurface remineralization and/or tubule mineralization.

In preferred embodiments of the product of this invention, the cationic and anionic parts each have a pH in water such that the mixed aqueous solution formed by mixing the parts with water and/or saliva has a pH of from about 4.5 to about 10.0.

Also in preferred embodiments, the product of this invention is substantially carbonate-free.

Another aspect of the present invention is directed to a method of remineralizing at least one subsurface lesion in a tooth and/or mineralizing at least one exposed dentinal tubule in a tooth, involving the steps of:

(i) providing the oral product of this invention;

(ii) mixing the cationic and anionic parts with water and/or saliva to form a mixed aqueous solution, the mixed aqueous solution having a pH of from about 4.5 to about 10.0, the mixed aqueous solution containing calcium ions released by the calcium salt (and divalent metal ions released by the divalent metal salt, if present) and phosphate ions released by the phosphate salt (and fluoride ions released by the fluoride salt, if present); and (iii) applying the mixed aqueous solution to the surface of the tooth promptly after formation of the solution in step (ii), the solution being applied to the surface of the tooth for a period of time sufficient to allow a remineralizing concentration of the calcium ions and a remineralizing concentration of the phosphate ions to diffuse through the tooth surface to a subsurface of the tooth, wherein at the subsurface the diffused calcium ions and the diffused phosphate ions react together to form an insoluble precipitate onto the subsurface lesion and/or the exposed dentinal tubule, thereby remineralizing the lesion and/or mineralizing the exposed tubule.

The product and method of this invention provide many advantages. For example, the product and method effect subsurface remineralization rather than surface remineralization. Since dental caries begins as a subsurface demineralization of the dental enamel, subsurface remineralization arrests and repairs the carious lesion before any permanent structural damage to the tooth occurs.

In addition, use of the product of this invention does not require preparation of the enamel surface, capping of the tooth, or removal of decay products. Furthermore, the product of this invention may be conveniently used by the public without Requiring a substantial change in dental care habits.

DETAILED DESCRIPTION OF THE INVENTION

The present invention is directed to two-part oral products and methods of using same to remineralize subsurface lesions in teeth, mineralize exposed dentinal tubules, and prevent demineralization of the teeth.

As used herein, the term "oral product" refers to a product which remains in the mouth for a relatively short period of time, wherein, while in the mouth, the product is in intimate contact with substantially all surfaces of the teeth. Non-limiting examples of oral products include toothpastes, prophylactic pastes, tooth polishes, gels, professional gels and other products applied by dentists, mouthwashes, mouthrinses, and the like.

The oral product of this invention contains (A) a discrete cationic part and (B) a discrete anionic part, the two parts being kept separate from one another until the product is ready to be used.

The cationic part of the product of this invention contains at least one water-soluble calcium salt.

As used herein with respect to the calcium salt(s), the term "/water-soluble" refers to a solubility in water such that the salt is capable of releasing at least about 1400 ppm by weight of ions into an aqueous solution having a temperature of about 25° C. and a pH of about 7.0.

Non-limiting examples of water-soluble calcium salts suitable for use in the product of this invention include, for example, calcium chloride, calcium lactate, calcium nitrate, calcium acetate, and calcium gluconate. Calcium lactate is preferred.

The cationic part contains an effective amount of the calcium salt(s). With respect to the amount of the calcium salt(s), the term "effective amount" means an amount which is sufficient to effect substantial remineralization of subsurface lesions and/or substantial mineralization of exposed dentinal tubules and substantial prevention of further demineralization. Preferably, the cationic part contains from about 0.05% to about 15%, more preferably from about 0.10% to about 10%, by weight of the calcium salt(s). Excess salt can be present, if desired.

In preferred embodiments of the product of this invention, the cationic part further contains an effective amount of at least one non-toxic, water-soluble salt of a divalent metal other than calcium. The presence of one or more divalent metal salts increases the stability of the mixed aqueous solution so as to further delay precipitation of the calcium, phosphate and (if present) fluoride ions until sufficient numbers of such ions have diffused through the tooth surface to the subsurface.

With respect to the divalent metal salt(s), the term "water-soluble" has the same meaning as given above with respect to the calcium salt(s).

With respect to the amount of the divalent metal salt, the term "effective amount" means that amount of the divalent metal salt which increases the stability of the mixed aqueous solution so as to further delay precipitation of the calcium, phosphate and fluoride ions until sufficient numbers of such ions have diffused through the tooth surface to the subsurface so as to effect substantial remineralization of subsurface lesions and/or mineralization of exposed dentinal tubules.

Preferably, the cationic part of the product of this invention contains at least about 0.001%, more preferably from about 0.001% to about 2.0%, by weight of the divalent metal salt(s).

As the stabilizing divalent metal salt, it is, in principle, possible to employ any water-soluble, non-toxic divalent metal compound which will stabilize the calcium and phosphate ions so that they do not rapidly or prematurely precipitate before diffusing into the teeth. In practice, however, it has been found that at least one member selected from the group consisting of magnesium, strontium, tin, and zinc, with magnesium being preferred, are the most effective in stabilizing the system.

Suitable magnesium compounds are, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds are, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds are, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds are, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

The anionic part of the product of this invention contains an effective amount of at least one water-soluble phosphate salt.

With respect to the phosphate salt(s), the terms "effective amount" and "water-soluble" have the same meanings as given above with respect to the calcium salt(s).

In preferred embodiments of the product of this invention, the concentration of the phosphate salt(s) is essentially the same as the concentration of the calcium salt(s). Thus, the anionic part preferably contains from about 0.05% to about 15%, more preferably from about 0.10% to about 10%, by weight of the phosphate salt(s). Excess phosphate salt can be used, if des red.

Suitable water-soluble phosphate salts for use in the present invention include, for example, alkali salts and ammonium salts of orthophosphoric acid, such as, e.g., potassium, sodium or ammonium orthophosphate; monopotassium phosphate; dipotassium phosphate; tripotassium phosphate; monosodium phosphate; disodium phosphate and trisodium phosphate.

If desired, water-soluble salts yielding both calcium and phosphate ions, such as monobasic calcium orthophosphate, may be employed in the product of this invention.

Also in preferred embodiments of the product of this invention, the anionic part further contains an effective amount of at least one water-soluble fluoride salt. The caries-prophylactic activity of fluoride salts has long been established. These salts are preferably present in the anionic part rather than in the cationic part so as to avoid formation of sparingly soluble calcium fluoride.

With respect to the fluoride salt(s), the terms "effective amount" and "water-soluble" have the same meanings as given above with respect to the calcium salt(s).

Preferably, the anionic part contains from about 0.01% to about 5.0%, more preferably from about 0.02% to about 2.0%, by weight of the fluoride salt(s).

Suitable water-soluble fluoride salts for use in the present invention include the alkali metal or ammonium fluorides such as sodium, potassium, lithium or ammonium fluoride; tin fluoride; indium fluoride; zirconium fluoride; copper fluoride; nickel fluoride; palladium fluoride; fluorozirconates such as sodium, potassium or ammonium fluorozirconate or tin fluorozirconate; fluorosilicates; fluoroborates; and fluorostannites. Although not preferred, fluorophosphates, such as sodium fluorophosphate, potassium fluorophosphate and ammonium fluorophosphate, are also suitable for use in the present invention. In addition, organic fluorides, such as the known amine fluorides, can also be used in the oral products of this invention.

Water-soluble alkali metal monofluorophosphates such as sodium monofluorophosphate, lithium monofluorophosphate and potassium monofluorophosphate, preferably sodium monofluorophosphate. In addition, other water-soluble monofluorophosphate salts may be employed including ammonium monofluorophosphate, aluminum monofluorophosphate, and the like. If monofluorophosphate salts are used as the fluoride source, they could be present in the cationic part along with the calcium salt without departing from the present invention. However, this is less desirable due to the potential loss of fluoride.

Sodium fluoride is the preferred fluoride salt for use in the present invention.

In preferred embodiments, the product of this invention is substantially carbonate-free, i.e., substantially free of carbonates and bicarbonates.

When the product of this invention is ready to be used, the cationic and anionic parts of the product are mixed and promptly applied to the teeth being treated.

The cationic and anionic parts may be mixed either in the oral cavity or immediately prior to their introduction into the oral cavity. If one or both of the cationic and anionic parts is disposed in an aqueous carrier, the two parts may be mixed together outside of the oral cavity and the resulting mixed aqueous solution then immediately introduced into the oral cavity to be admixed with saliva, the resulting mixed aqueous solution then being applied to the teeth. Alternatively, the cationic and anionic parts may be introduced into the oral cavity, where the two parts are combined simultaneously with one another and with the saliva to form the mixed aqueous solution used to treat the teeth in accordance with the present invention. With a toothpaste, gel, prophylaxis paste and the like, mixing of the cationic and anionic parts is achieved on the tooth surface while brushing.

Upon preparation with water or upon use in the oral cavity, the mixed aqueous solution used in the present invention should have a pH of from about 4.5 to about 10.0, preferably from about 5.0 to about 7.0, most preferably from about 5.5 to about 6.5, before and after the precipitation reaction, and be otherwise compatible in the oral environment. At a pH within such range, enough of the calcium ions, phosphate ions and, if present, fluoride ions in the mixed aqueous solution remain soluble for the period of time required to allow sufficient amounts of the ions to diffuse through the tooth surface so as to substantially remineralize the subsurface lesions and/or substantially mineralize the exposed tubules of the dental enamel. If the mixed aqueous solution has a pH below about 3, demineralization will occur rapidly. A pH below about 2.5 is undesirable from a safety standpoint. The pH of the mixed aqueous solution may be adjusted to the desired pH by methods well known in the art. The pH may be lowered by the addition of any acid which is safe for use in the oral cavity and which yields the desired pH at the amount employed. Examples of suitable acids include acetic acid, phosphoric acid, citric acid and malic acid.

In the method of this invention, the mixed aqueous solution is applied to the surface of the tooth for a period of time sufficient to allow a remineralizing concentration of the calcium ions and a remineralizing concentration of the phosphate ions to simultaneously diffuse through the tooth surface to a subsurface of the tooth, wherein at the subsurface the diffused calcium ions and the diffused phosphate ions react together to form an insoluble precipitate onto the subsurface lesion and/or the exposed dentinal tubule, thereby remineralizing the lesion and/or mineralizing the exposed tubule. With respect to the respective amounts of the dissolved calcium ions and dissolved phosphate ions which are allowed to diffuse through the tooth surface, the term "remineralizing concentration" means that amount of the dissolved calcium ions and that amount of the dissolved phosphate ions which will provide substantial remineralization of the subsurface lesion(s) and/or substantial mineralization of the exposed dentinal tubule(s).

To effect substantial remineralization of subsurface lesions and/or mineralization of exposed dentinal tubules, the amount of the mixed aqueous solution placed in the mouth should contain at least about 100 ppm of desired cations and 100 ppm of desired anions and preferably contains more than 1000 ppm of desired cations and 1000 ppm of desired anions. The solution preferably contains at least 10 ppm, more preferably greater than 100 ppm, of divalent metal ions other than calcium. Also preferably, the mixed aqueous solution placed in the mouth contains from about 20 ppm to about 5000 ppm of fluoride ions.

Typically, at least about 10 seconds is required for diffusion of the remineralizing concentration of the calcium and phosphate ions. Preferably, he length of time of contact between the mixed aqueous solution and the teeth being treated should be greater than 30 seconds and even longer if possible.

The mixed aqueous solution used in the present invention simultaneously delivers the calcium ions, the phosphate ions, and, if present, the fluoride ions to the tooth surface. This in turn allows the cations and anions to simultaneously diffuse through the tooth surface to the subsurface. This is in contrast to the systems taught in U.S. Pat. Nos. 4,083,955 (Grabenstetter et al.) and 4,397,837 (Raaf et al.), which were discussed previously herein, wherein the cations and anions are caused to diffuse sequentially through the tooth surface to the subsurface.

The cationic and anionic parts and the mixed aqueous solution formed therefrom should each be compatible in the oral environment. While some precipitation may occur, not all of the ions should combine prematurely in the solution to form a precipitate, but must be able to diffuse through the surface of the tooth to a demineralized subsurface area and be able to form an insoluble salt.

Furthermore, the mixed aqueous solution, the cationic and anionic parts, and the insoluble precipitates formed therefrom, must have acceptable levels of toxicity (i.e., the particular ions, in the amounts used in the remineralization process, must be non-toxic).

In the oral product of this invention, the cationic and anionic parts are kept separate from one another until the product is to be used. Separation of the cationic and anionic parts may be achieved by various means.

For example, the cationic and anionic parts of the products of this invention may be kept separate from each other by disposing the parts as separate layers in a multilayer product, for example, a two-layer toothpaste, a two-layer gel, a two-layer mouthwash, a two-layer chewing gum, and the like.

In a particularly preferred embodiment of the invention, separation of the cationic and anionic parts is achieved by having either the first pharmaceutically acceptable carrier or the second pharmaceutically acceptable carrier be in the form of an aqueous carrier and the other carrier be in the form of a hydrophilic, non-aqueous carrier.

As used herein, the term "pharmaceutically acceptable carrier" means a suitable vehicle which can be used to apply the oral products of this invention in the oral cavity. Examples of pharmaceutically acceptable carriers include liquid carrier compositions such as topical solutions, mouthwashes, toothpastes, prophylaxis pastes, mouthrinses, professional gels, dental gels, and the like.

Examples of suitable hydrophilic, non-aqueous carriers which can be used in the present invention include non-aqueous solvents such as, e.g., ethyl alcohol, glycerine and propylene glycol. A particularly preferred hydrophilic, non-aqueous carrier is a polyethylene oxide having a molecular weight of about 400 (also known under the designation "Carbowax 400").

In a particularly preferred embodiment of a toothpaste product of this invention, the cationic part and the anionic part are disposed as two discrete stripes intertwined with one another, wherein one stripe contains the cationic part and has one color, and the other stripe contains the anionic part and has a second color. One or both of the stripes is non-aqueous and hydrophilic. In addition, one stripe may have a paste-like consistency and the other stripe may have a gel-like consistency.

In another suitable embodiment of the product of this invention, the product is in the form of an emulsion or dispersion wherein the cationic and anionic parts are present in different phases.

It is further possible to provide one or both of the cationic and anionic parts with a coating (that is to say, encapsulate it), this coating being such as only to release the active substance through the action of heat or through mechanical action. Examples of suitable encapsulation materials include, e.g., shellac; waxes; fats; vinylpyridine; alkyl vinylpyridine and polymers/copolymers of other vinyl monomers; ethyl cellulose, benzyl cellulose, cellulose acetobutyrate and other cellulose derivatives; polyvinyl acetal diethylaminoacetate and dimethylaminoethyl methacrylate/methyl methacrylate copolymers; and the like.

Separation may also be achieved by disposing the two parts in a single carrier, wherein the single carrier is non-aqueous and hydrophilic and capable of simultaneously releasing the two parts upon contact with water.

Yet another way to separate the cationic and anionic parts is to dispose the cationic part in a first carrier and the anionic part in a second carrier, wherein the first carrier is composed of a material in which the anionic part is insoluble but the cationic part is soluble, further wherein the second carrier is composed of a material in which the cationic part is insoluble but the anionic part is soluble.

Of course, the cationic and anionic parts may also be separated by a physical barrier such as, for example, when the two parts are disposed in separate compartments of a two-compartment container, e.g., two-compartment tube or two-compartment aerosol can. In this embodiment, the two compartments are kept separate from one another during storage but are preferably dispensed simultaneously with one another from the container. With respect to toothpastes, gels, creams and the like within the scope of this invention, a plurality of packaging methods may be employed in order to separately contain or store the cationic and anionic parts and provide effective dispensing thereof into the oral cavity.

Thus, the cationic and anionic parts may be simultaneously dispensed from separate collapsible tubes preferably made of plastic, a plastic and metal laminate, etc. For convenience and in order to aid in dispensing substantially equal amounts of the parts, the tubes may be held together by banding or cementing, preferably along the corresponding ventral sides of the tubes. In another embodiment, the two tubes may be constructed to have abutting, preferably flat, sidewall portions. In the foregoing embodiments, the mouths of the tubes are usually sufficiently close so that sufficient quantities of the cationic and anionic parts of the toothpaste or gel may be simultaneously dispensed directly on the toothbrush with the tubes being capped separately.

Alternatively, another packaging method involves loading the cationic and anionic parts of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and anionic parts, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of the outer tube and the mouth of the inner tube. The closures of this tube-within-a-tube (which can screw on the outer tube or simply be held by pressure) may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement is a pressurized container which is provided with two compartments and two spouts. The internal pressure of the compartments is maintained by a pressurized gas, i.e., nitrogen, at the bottom of each compartment. Operation of a mechanical actuator actuates valves which release the contents of the compartments through the spouts, causing discharge of the paste or gel components onto a brush.

The mouthwash, rinse or similar liquid embodiments are maintained in a manner similar to the pastes or gels in that, during storage, each of the cationic and anionic parts are maintained separate from one another to prevent premature reaction. Upon dispensing, the cationic and anionic parts mix and react in the oral cavity to effect remineralization of dental enamel. The liquid cationic and anionic parts can therefore be stored each in separate compartments of a dual-compartment dispenser. The dispenser usually includes a closure system containing, for example, an inclined crown portion, at least two pouring spouts extending upwardly from an upper surface of the crown portion, and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve a window function for gauging the amounts of liquid remaining in the dispenser. The walls of the containers can be scribed or otherwise calibrated to assist in dispensing the correct remineralizing amount of the mixed aqueous composition.

The first and second pharmaceutically acceptable carriers used in the product of this invention may contain other ingredients in addition to the cationic and anionic salts described previously herein. For example, in the case of toothpastes and prophylaxis pastes, suitable pharmaceutically acceptable carriers contain cleaning and polishing agents and other constituents ordinarily provided in dentifrices and prophylaxis pastes. In the case of topical solutions and mouthwashes, suitable carriers include water and other liquids.

In general, the pharmaceutically acceptable carrier component used in the oral products of this invention contains abrasive polishing materials, surfactants, flavoring agents and/or sweetening agents. Additional carrier ingredients will depend on the particular type of carrier.

Non-limiting examples of suitable polishing agents for use in the pharmaceutically acceptable carrier component of the oral products of this invention include calcium carbonate, silica xerogels, insoluble sodium metaphosphate, and various calcium phosphates such as, e.g., dicalcium phosphate, tricalcium phosphate, calcium pyrophosphate, and the like.

The oral product of this invention may contain up to about 90% by weight of the polishing agent(s). Preferably, the oral product contains from about 5% to about 60%, more preferably from about 20% to about 50%, and most preferably from about 25% to about 45%, by weight of the polishing agent(s).

Suitable surfactants for use in the pharmaceutically acceptable carrier component of the oral products of this invention may be non-ionic, anionic, cationic or ampholytic in nature. Suitable surfactants include, but are not limited to, water-soluble alkyl sulfates having from about 8 to about 18 carbon atoms in the alkyl radical, such as sodium lauryl sulfate; water-soluble salts of sulfonated monoglycerides of fatty acids having from about 10 to about 18 carbon atoms in the alkyl radical such as sodium coconut monoglyceride sulfonate, salts of fatty acid amides of taurines such as sodium-N-methyl palmitoyl taurine, and salts of fatty acid esters of isethionic acid. Other particularly suitable surfactants include non-ionic surfactants such as condensates of sorbitan monostearate and ethylene oxide, copolymers of the poly(oxypropylene)-poly(oxyethylene) type and amphoteric agents such as quaternized imidazole derivatives. Useful cationic surfactant germicides and antibacterial compounds include tertiary amines containing one fatty alkyl group and two poly(oxyethylene) groups, benzyldimethyl stearyl ammonium chloride, and di-isobutylphenoxyethoxyethyl dimethyl benzyl ammonium chloride.

Surfactants are preferably used in the oral products of this invention in an amount ranging from about 0.05% to about 10.0%, more preferably from about 0.5% to about 5%, by weight of the oral product.

Suitable flavoring agents which may be used in the carrier component of the oral products of this invention include, for example, oil of wintergreen, oil of peppermint, menthol, oil of spearmint, oil of sassafras, and oil of clove.

Suitable sweetening agents for use in the carrier component include, e.g., aspartame, acesulfame, saccharin, dextrose, levulose, sodium cyclamate, and mixtures of sugar and a sweetener such as sucralose.

The oral products of this invention preferably contain from about 0.005% to about 2% by weight of flavoring and/or sweetening agents.

In addition to the foregoing carrier ingredients, carrier components for toothpaste embodiments of the oral products of this invention preferably further contain a combination of thickening agents, humectants, and water.

One or more thickening agents (i.e., binder agents) are added to the carrier component of the toothpaste embodiments of this invention in order to provide the toothpastes with a desirable consistency. Suitable thickening agents include, e.g., water-soluble salts of cellulose ethers, such as, for example, sodium carboxymethyl cellulose, hydroxypropyl cellulose, and hydroxyethyl cellulose. Natural gums such as gum karaya, gum arabic, carreegeenan and gum tragacanth, can also be used. Colloidal magnesium aluminum silicate, silica aerogels, silica xerogels, fumed silica, or other finely divided silica can be used as part of the thickening agent in a toothpaste formulation for further improved texture. A preferred thickening agent for toothpastes is xanthan gum.

The toothpaste form of the oral product of this invention may contain from about 0.5% to about 5.0% by weight of a thickening agent(s).

It is also desirable to include some humectant material in a toothpaste to keep it from hardening. Suitable humectants include, e.g., glycerol, sorbitol, propylene glycols, polyethylene glycols, other edible polyhydric alcohols, and mixtures of the foregoing.

A humectant may constitute up to about 65% by weight of the oral product of this invention.

It is also possible to manufacture the oral product of this invention in the form of a transparent or translucent gel. This is accomplished by matching the refractive index of the water-humectant system with the abrasives and inorganic thickeners if used.

Professional gels can be formulated similar to toothpastes except with higher fluoride concentrations. Since professional gels are not designed for cleaning but only for applying fluoride, abrasives and other cleaning agents need not be included in the professional gel formulations of this invention.

Transparent gel embodiments of the oral products of this invention preferably contain at least one gel-forming agent. Suitable gel-forming agents usually include known thickeners such as, e.g., the alkali salts of polyacrylic acid and dehydrated silicon dioxide gels of particle size of from about 2 to about 20 microns and specific surface area of from about 200 to about 900 square meters per gram.

Mouthwashes and mouthrinses generally contain an aqueous solution of ethyl alcohol and flavoring agents. The alcohol provides an antibacterial effect, solubilizes the flavoring agents, and provides a pleasant mouth feeling. Alcohol-free mouthwashes are now, however, gaining in popularity. Optionally, mouthwashes and mouthrinses may also contain additional antibacterial agents and humectants such as glycerine and sorbitol which give a moist feeling to the mouth.

The carrier portion of the mouthwash embodiments of the oral products of this invention preferably contains a water/ ethyl alcohol solution (at a water:ethyl alcohol volume ratio of from about 20:1 to about 2:1), at least one water-soluble fluoride salt, at least one flavoring agent, at least one sweetener, at least one humectant, and at least one emulsifier-surfactant. Preferably, the carrier portion of the mouthwash embodiments of the present invention contains from about 0% to about 30%, more preferably from about 0% to about 20%, by weight of ethyl alcohol; from about 0% to about 20% by weight of glycerine or other humectant; from about 30% to about 90% by weight of water; from about 0% to about 0.1% by weight of an antibacterial agent; from about 0% to about 0.2% by weight of a soluble fluoride source; from about 0.1% to about 0.5% by weight of a sweetening agent; from about 0.01% to about 2.0% by weight of a flavoring agent; and from about 0.1% to about 1% by weight of an emulsifier-surfactant.

Any of the water-soluble fluoride salts, flavoring agents, sweeteners, humectants and surfactants previously disclosed herein may be used in the mouthwash embodiments of the oral products of this invention.

The insoluble precipitate formed from the diffused calcium and phosphate ions at the subsurface lesion(s) and/or exposed dentinal tubule(s) in accordance with the present invention is a calcium phosphate or a hydroxyapatite (the natural constituent of tooth enamel). If diffused fluoride ions are present, the precipitate will have fluoride ions incorporated therein. The fluoride ions will render the remineralized enamel more resistant to demineralization than was the original enamel. Therefore, if the mixed aqueous solution used in the present invention contains at least one water-soluble fluoride salt, the mixed aqueous solution will not only remineralize the enamel but will also render such enamel more resistant to subsequent demineralization than was the original enamel.

The following Examples illustrate the invention. In the Examples and elsewhere herein, parts and percentages are by weight unless otherwise stated.

EXPERIMENTAL

EXAMPLE 1

Artificial lesions, about 50 µ deep, were formed in one surface of bovine enamel chips using a demineralizing Carbopol gel, which was used to treat the specimens for 72 hours. The surface hardness of the surface to be treated was then measured.

The regimen cycle consisted of a 30-minute demineralization in a standard demineralizing solution followed by a 5-minute treatment of the test products diluted 1 part product to two parts human saliva, followed by a 60-minute remineralization in human saliva. Overnight, which was every fifth cycle, the specimens were kept with a layer of saliva and stored in a cold room. The test ran for three days, for a total of 15 demineralization:treatment:remineralization cycles.

For the treatment cycle, the two parts of the remineralizing test agents of the example were separately diluted 1 part product to 2 parts saliva and mixed together immediately before immersion of the enamel specimens.

The two-part oral remineralizing product had the formulation set forth in Table I:

TABLE I

Example 1: Formulation

| | Part A | Part B |
|---|---|---|
| Water | 71 | 66.45 |
| Calcium Nitrate | 4 | 0.00 |
| Dipotassium phosphate | | 8.00 |
| Sodium Fluoride | | 0.55 |
| Glycerin | 25 | 25.00 |
| Acetic Acid | \multicolumn{2}{c}{To adjust pH of A & B mixture of 5.5 immediately after mixing.} |

The increases in hardness and fluoride levels occurring in Example 1 are set forth in Tables II and III.

TABLE II

Example 1:
HARDNESS INCREASE DUE TO TREATMENT
(Vickers Hardness Units)

| | Example 1 | Crest | 1200 ppm Fluoride at pH 5.5 | Placebo |
|---|---|---|---|---|
| 5 cycles | 17.0 ± 1.9 | 11.8 ± 1.4 | | |
| 10 cycles | 23.6 ± 1.4 | 13.0 ± 3.6 | 13.7 ± 2.3 | 3.9 ± 0.7 |
| 15 cycles | 34.8 ± 2.8 | 11.2 ± 1.7 | | |
| 20 cycles | 48.2 ± .2.8 | 17.5 ± 2.2 | | |

TABLE III

Example 1:
FLUORIDE INCREASE DUE TO TREATMENT
($\mu$g/cm$^3$)

| | Example 1 | Crest | 1200 ppm Fluoride at pH 5.5 | Placebo |
|---|---|---|---|---|
| 5 cycles | 2433 | 1879 | | |
| 10 cycles | 3523 | 2082 | 2928 | 244 |
| 15 cycles | 4431 | 2196 | | |
| 20 cycles | 4749 | 2964 | | |

The results presented in Tables II and III show much greater remineralization, as measured by hardness increase and fluoride uptake, due to treatment with the product of Example 1 than with Crest, the fluoride solution or the placebo.

EXAMPLES 2, 3 and 4

Two-part oral remineralizing treatments were prepared having the formulations shown in Table IV:

TABLE IV

Example 2–4: Formulations

| | Part A | Part B |
|---|---|---|
| | \multicolumn{2}{c}{Example 2} | |
| Water | 73 | 66.45 |
| Calcium Nitrate | 2 | 0.00 |
| Dipotassium phosphate | | 8.00 |
| Sodium Fluoride | | 0.55 |
| Glycerin | 25 | 25.00 |

TABLE IV-continued

Example 2–4: Formulations

|  | Part A | Part B |
|---|---|---|
| Acetic Acid | | To adjust pH of A & B mixture of 5.5 immediately after mixing. |

Example 3

|  | Part A | Part B |
|---|---|---|
| Water | 74 | 66.45 |
| Calcium Nitrate | 1 | 0.00 |
| Dipotassium phosphate | | 8.00 |
| Sodium Fluoride | | 0.55 |
| Glycerin | 25 | 25.00 |
| Acetic Acid | | To adjust pH of A & B mixture of 5.5 immediately after mixing. |

Example 4

|  | Part A | Part B |
|---|---|---|
| Water | 73 | 66.45 |
| Calcium Nitrate | 2 | 0.00 |
| Dipotassium phosphate | | 8.00 |
| Sodium Fluoride | | 0.55 |
| Glycerin | 25 | 25.00 |
| Acetic Acid | | To adjust pH of A & B mixture of 5.5 immediately after mixing. |

The same cyclic regimen used to evaluate Example 1 was used to evaluate the remineralizing efficacy of the above formulations compared with Crest. In this study, 15 cycles were used.

The increases in hardness and fluoride levels are presented in Table V.

TABLE V

Examples 2–4: HARDNESS AND FLUORIDE INCREASE DUE TO TREATMENT

|  | Example 2 | Example 3 | Example 4 | Crest |
|---|---|---|---|---|
| Hardness Increase | 45.1 ± 2.9 | 37.6 ± 2.4 | 32.7 ± 2.5 | 14.2 ± 1.8 |
| Fluoride Uptake | 4677 ± 219 | 5686 ± 138 | 4495 ± 343 | 2099 ± 182 |

The results presented in Table V show much greater remineralization, as measured by hardness increase and fluoride uptake, due to treatment with Examples 2, 3, and 4 of the invention than with Crest.

EXAMPLES 5–10

Two-part oral remineralizing treatments having the formulations set forth in Table VI were prepared:

TABLE VI

Examples 5–10: Formulations

|  | Part A | Part B |
|---|---|---|
| Example 5 | | |
| Water | 71.2 | 70.45 |
| Calcium Nitrate | 3.8 | 0.00 |
| Dipotassium phosphate | | 4.00 |
| Sodium Fluoride | | 0.55 |
| Glycerin | 25 | 25.00 |
| Acetic Acid | | To adjust pH of A & B mixture of 5.5 immediately after mixing. |
| Example 6 | | |
| Water | 67.4 | 66.86 |
| Calcium Nitrate | 7.6 | 0.00 |
| Dipotassium phosphate | | 8.00 |
| Sodium Fluoride | | 0.14 |
| Glycerin | 25 | 25.00 |
| Acetic Acid | | To adjust pH of A & B mixture of 5.5 immediately after mixing. |
| Example 7 | | |
| Water | 67.4 | 66.45 |
| Calcium Nitrate | 7.6 | 0.00 |
| Dipotassium phosphate | | 8.00 |
| Sodium Fluoride | | 0.55 |
| Glycerin | 25 | 25.00 |
| Acetic Acid | | To adjust pH of A & B mixture of 5.5 immediately after mixing. |
| Example 8 | | |
| Water | 63.6 | 62.45 |
| Calcium Nitrate | 11.4 | 0.00 |
| Dipotassium phosphate | | 12.00 |
| Sodium Fluoride | | 0.55 |
| Glycerin | 25 | 25.00 |
| Acetic Acid | | To adjust pH of A & B mixture of 5.5 immediately after mixing. |
| Example 9 | | |
| Water | 67.4 | 66.45 |
| Calcium Nitrate | 11.4 | 0.00 |
| Dipotassium phosphate | | 8.00 |
| Sodium Fluoride | | 0.55 |
| Glycerin | 25 | 25.00 |
| Acetic Acid | | To adjust pH of A & B mixture of 5.5 immediately after mixing. |
| Example 10 | | |
| Water | 67.4 | 66.45 |
| Calcium Nitrate | 7.6 | 0.00 |
| Dipotassium phosphate | | 8.00 |
| Sodium Fluoride | | 0.55 |
| Glycerin | 25 | 25.00 |
| Acetic Acid | | To adjust pH of A & B mixture of 5.5 immediately after mixing. |

The same cyclic regimen used to evaluate Examples 1–4 was used to evaluate the remineralizing efficacy of the Examples 5–10 compared with Crest. In this study, 15 cycles were used. The increase in hardness is shown in Table VII.

TABLE VII

Examples 5–10: HARDNESS INCREASE DUE TO TREATMENT Vickers Hardness Units

|  | Hardness Increase |
|---|---|
| Example 5 | 97 ± 6 |
| Example 6 | 97 ± 6 |
| Example 7 | 95 ± 2 |
| Example 8 | 84 ± 5 |
| Example 9 | 83 ± 5 |
| Example 10 | 82 ± 3 |
| Crest | 20 ± 2 |

The results presented in Table VII show much greater remineralization, as measured by hardness increase, due to treatment with Examples 5–10 of the invention than with Crest. Example 6 shows that even when the fluoride concentration is lowered to supply only 27 percent of that supplied by Crest (i.e., 275 ppm versus 1150 ppm) much higher levels of remineralization are still achieved.

EXAMPLES 11–16

Examples 11–16 illustrate various embodiments of remineralizing toothpaste formulations of the invention as presented in Table VIII:

TABLE VIII

Examples 11–16: Formulations

|  | Part A | Part B |
|---|---|---|
| Example 11 | | |
| Glycerin | 10.0 | 10.0 |
| Sorbitol | 40.0 | 40.0 |
| Water | 18.5 | 19.32 |
| Silica abrasive | 15.0 | 15.0 |
| Silica thickener | 8.0 | 8.0 |
| DCPDH | 0.0 | 0.0 |
| Calcium Nitrate | 5.0 | 0.0 |
| Monosodium Phosphate | 0.0 | 3.7 |
| Sodium Metaphosphate | 0.0 | 0.0 |
| CMC | 1.0 | 1.0 |
| Sodium Lauryl Sulfate | 1.5 | 1.5 |
| Sodium Fluoride | 0.0 | 0.48 |
| Flavor | 0.8 | 0.8 |
| Saccharin | 0.2 | 0.2 |
| Example 12 | | |
| Glycerin | 5.0 | 4.0 |
| Sorbitol | 30.0 | 30.0 |
| Water | 17.9 | 14.82 |
| Silica abrasive | 0.0 | 0.0 |
| Silica thickener | 0.0 | 0.0 |
| DCPDH | 40.0 | 0.0 |
| Calcium Nitrate | 3.5 | 0.0 |
| Monosodium Phosphate | 0.0 | 6.5 |
| Sodium Metaphosphate | 0.0 | 40.0 |
| CMC | 1.2 | 1.5 |
| Sodium Lauryl Sulfate | 1.2 | 1.8 |
| Sodium Fluoride | 0.0 | 0.48 |
| Flavor | 0.9 | 0.7 |
| Saccharin | 0.3 | 0.2 |
| Example 13 | | |
| Glycerin | 6.0 | 6.0 |
| Sorbitol | 34.0 | 30.0 |
| Water | 32.3 | 29.5 |
| Silica abrasive | 10.0 | 5.0 |
| Silica thickener | 8.0 | 5.0 |
| DCPDH | 0.0 | 0.0 |
| Calcium Nitrate | 6.0 | 0.0 |
| Monosodium Phosphate | 0.0 | 10.0 |
| Sodium Metaphosphate | 0.0 | 10.0 |
| CMC | 1.4 | 1.5 |
| Sodium Lauryl Sulfate | 1.3 | 1.5 |
| Sodium Fluoride | 0.0 | 0.1 |
| Flavor | 0.7 | 1.0 |
| Saccharin | 0.3 | 0.4 |
| Example 14 | | |
| Glycerin | 10.0 | 10.0 |
| Sorbitol | 40.0 | 40.0 |
| Water | 18.5 | 19.32 |
| Silica abrasive | 15.0 | 15.0 |
| Silica thickener | 8.0 | 8.0 |
| DCPDH | 0.0 | 0.0 |
| Calcium Nitrate | 5.0 | 0.0 |
| Monosodium Phosphate | 0.0 | 3.7 |
| Sodium Metaphosphate | 0.0 | 0.0 |

TABLE VIII-continued

Examples 11–16: Formulations

|  | Part A | Part B |
|---|---|---|
| CMC | 1.5 | 1.5 |
| Sodium Lauryl Sulfate | 0.0 | 1.81 |
| Sodium Fluoride | 0.0 | 0.0 |
| Flavor | 0.8 | 0.8 |
| Saccharin | 0.2 | 0.2 |
| Example 15 | | |
| Glycerin | 5.0 | 4.0 |
| Sorbitol | 30.0 | 30.0 |
| Water | 17.9 | 14.82 |
| Silica abrasive | 0.0 | 0.0 |
| Silica thickener | 0.0 | 0.0 |
| DCPDH | 40.0 | 0.0 |
| Calcium Nitrate | 3.5 | 0.0 |
| Monosodium Phosphate | 0.0 | 6.5 |
| Sodium Metaphosphate | 1.2 | 1.5 |
| CMC | 1.2 | 1.8 |
| Sodium Lauryl Sulfate | 0.0 | 0.0 |
| Sodium Fluoride | 0.0 | 1.52 |
| Flavor | 0.9 | 0.7 |
| Saccharin | 0.3 | 0.2 |
| Example 16 | | |
| Glycerin | 6.0 | 6.0 |
| Sorbitol | 34.0 | 30.0 |
| Water | 32.3 | 29.5 |
| Silica abrasive | 10.0 | 5.0 |
| Silica thickener | 8.0 | 5.0 |
| DCPDH | 0.0 | 0.0 |
| Calcium Nitrate | 6.0 | 0.0 |
| Monosodium Phosphate | 0.0 | 10.0 |
| Sodium Metaphosphate | 1.4 | 1.5 |
| CMC | 1.3 | 1.5 |
| Sodium Lauryl Sulfate | 0.0 | 0.0 |
| Sodium Fluoride | 0.0 | 0.2 |
| Flavor | 0.7 | 1.0 |
| Saccharin | 0.3 | 0.4 |

EXAMPLE 17

Example 17 illustrates an embodiment of a remineralizing mouthwash formulation as set forth in Table IX:

TABLE IX

Example 17: Formulation

|  | Part A | Part B |
|---|---|---|
| Glycerin | 10.000 | 10.0 |
| Ethanol | 20.000 | 20.0 |
| Sodium Fluoride | 0.055 | 0.00 |
| Calcium Nitrate | 0.000 | 5.00 |
| Dipotassium Phosphate | 5.000 | 0.00 |
| Monopotassium Phosphate | 0.000 | 0.00 |
| Water | qs | qs |

EXAMPLES 18–21

Examples 18–21 illustrate various toothpaste products within the scope of the present invention. The formulations of these toothpaste products are shown in Table X.

TABLE X

Examples 18–21: Formulations

Example 18

Part A

| | |
|---|---|
| Glycerine | 6.5 |
| Methyl Paraben | 0.025 |
| Propyl Paraben | 0.025 |
| CMC | 0.25 |
| Xanthan Gum | 0.5 |
| Water | 19.925 |
| Sorbitol (70% Sol'n) | 10 |
| Titanium Dioxide | 0.1 |
| Sodium Saccharin | 0.3 |
| Magnesium Chloride | 0.5 |
| Calcium lactate Pentahydrate | 0.875 |
| Hydrated Silica Abrasive | 7 |
| Hydrated Silica Thickener | 3 |
| Flavor | 0.5 |
| Tween 20 | 0.5 |

Part B

| | |
|---|---|
| Glycerine | 12.5 |
| PEG 8 | 1 |
| CMC | 0.25 |
| Xanthan Gum | 0.5 |
| Water | 20.7 |
| Titanium Dioxide | 0.1 |
| Sodium Fluoride | 0.25 |
| Sodium Saccharin | 0.3 |
| Monoammonium Phosphate | 2.45 |
| Hydrated Silica Abrasive | 9 |
| Hydrated Silica Thickener | 1.5 |
| Flavor | 0.35 |
| Tween 20 | 0.35 |
| Sodium Lauryl Sulfate | 0.75 |
| TOTAL | 100.00 |

Example 19

Part A

| | |
|---|---|
| Glycerine | 10 |
| Methyl Paraben | 0.025 |
| Propyl Paraben | 0.025 |
| CMC | 0.25 |
| Xanthan Gum | 0.5 |
| Water | 20.2 |
| Sorbitol (70% Sol'n) | 6.5 |
| Titanium Dioxide | 0.1 |
| Sodium Saccharin | 0.3 |
| Magnesium Chloride | 0.6 |
| Calcium Acetate Monohydrate | 0.5 |
| Hydrated Silica Abrasive | 7 |
| Hydrated Silica Thickener | 3 |
| Flavor | 0.5 |
| Tween 20 | 0.5 |

Part B

| | |
|---|---|
| Glycerine | 12.5 |
| CMC | 0.25 |
| Xanthan Gum | 0.5 |
| Water | 18.05 |
| Sorbitol (70% sol'n) | 5 |
| Titanium Dioxide | 0.1 |
| Sodium Fluoride | 0.25 |
| Sodium Saccharin | 0.3 |
| Monoammonium Phosphate | 1.1 |
| Hydrated Silica Abrasive | 9 |
| Hydrated Silica Thickener | 1.5 |
| Flavor | 0.35 |
| Tween 20 | 0.35 |
| Sodium Lauryl Sulfate | 0.75 |
| TOTAL | 100.00 |

Example 20

Part A

| | |
|---|---|
| Glycerine | 7.5 |
| Methyl Paraben | 0.025 |
| Propyl Paraben | 0.025 |
| CMC | 0.4 |
| Xanthan Gum | 0.3 |
| Water | 19.5 |
| Sorbitol (70% Sol'n) | 7.5 |
| Titanium Dioxide | 0.1 |
| Sodium Saccharin | 0.3 |
| Magnesium Chloride | 2 |
| Calcium lactate Pentahydrate | 1.75 |
| Hydrated Silica Abrasive | 7 |
| Hydrated Silica Thickener | 2.5 |
| Flavor | 0.4 |
| Tween 20 | 0.4 |
| Sodium Lauryl Sulfate | 0.3 |

Part B

| | |
|---|---|
| Glycerine | 7.5 |
| PEG 8 | 1 |
| CMC | 0.25 |
| Xanthan Gum | 0.4 |
| Water | 18.85 |
| Sorbitol (70% sol'n) | 7.5 |
| Titanium Dioxide | 0.1 |
| Sodium Fluoride | 0.25 |
| Sodium Saccharin | 0.3 |
| Monoammonium Phosphate | 2.8 |
| Hydrated Silica Abrasive | 7 |
| Hydrated Silica Thickener | 2.75 |
| Flavor | 0.4 |
| Tween 20 | 0.4 |
| Sodium Lauryl Sulfate | 0.5 |
| TOTAL | 100.00 |

Example 21

Part A

| | |
|---|---|
| Glycerine | 7.5 |
| Methyl Paraben | 0.025 |
| Propyl Paraben | 0.025 |
| CMC | 0.4 |
| Xanthan Gum | 0.3 |
| Water | 17.55 |
| Sorbitol (70% Sol'n) | 10 |
| Titanium Dioxide | 0.1 |
| Sodium Saccharin | 0.3 |
| Magnesium Chloride | 2 |
| Calcium Acetate Monohydrate | 1 |

TABLE X-continued

Examples 18–21: Formulations

| | |
|---|---|
| Hydrated Silica Abrasive | 7 |
| Hydrated Silica Thickener | 2.5 |
| Flavor | 0.4 |
| Tween 20 | 0.4 |
| Sodium Lauryl Sulfate | 0.5 |
| Part B | |
| Glycerine | 7.5 |
| PEG 8 | 1 |
| CMC | 0.25 |
| Xanthan Gum | 0.4 |
| Water | 18.95 |
| Sorbitol (70% sol'n) | 7.5 |
| Titanium Dioxide | 0.1 |
| Sodium Fluoride | 0.25 |
| Sodium Saccharin | 0.3 |
| Monoammonium Phosphate | 2.8 |
| Hydrated Silica Abrasive | 7 |
| Hydrated Silica Thickener | 2.75 |
| Flavor | 0.4 |
| Tween 20 | 0.4 |
| Sodium Lauryl Sulfate | 0.4 |
| TOTAL | 100.00 |

EXAMPLES 22–24

Examples 22–24 illustrate mouthrinse products within the scope of the present invention. The formulations of these products are set forth in Table XI.

TABLE XI

Examples 22–24: Formulations

| | Example 22 |
|---|---|
| Part A | |
| Methyl Paraben | 0.025 |
| Propyl Paraben | 0.025 |
| Water | 40.67 |
| Sorbitol 70% sol'n | 7.5 |
| Sodium Saccharin | 0.175 |
| Magnesium Chloride | 0.5 |
| Calcium Lactate Pentahydrate | 0.875 |
| Flavor | 0.035 |
| Tween 20 | 0.095 |
| Sodium Lauryl Sulfate | 0.1 |
| Part B | |
| Water | 41.065 |
| Sorbitol 70% sol'n | 7.5 |
| Sodium Fluoride | 0.05 |
| Sodium Saccharin | 0.15 |
| Monoammonium Phosphate | 1.1 |
| Flavor | 0.035 |
| Tween 20 | 0.1 |
| TOTAL | 100.00 |

TABLE XI-continued

Examples 22–24: Formulations

| | Example 23 |
|---|---|
| Part A | |
| Glycerine | 5 |
| Methyl Paraben | 0.025 |
| Propyl Paraben | 0.025 |
| Ethanol | 5 |
| Water | 33.57 |
| Sorbitol 70% sol'n | 5 |
| Sodium Saccharin | 0.15 |
| Magnesium Chloride | 0.5 |
| Calcium Acetate Monohydrate | 0.5 |
| Flavor | 0.035 |
| Tween 20 | 0.095 |
| Sodium Lauryl Sulfate | 0.1 |
| Part B | |
| Water | 38.9 |
| Ethanol | 5 |
| Sorbitol 70% sol'n | 5 |
| Sodium Fluoride | 0.05 |
| Sodium Saccharin | 0.15 |
| Monoammonium Phosphate | 0.75 |
| Flavor | 0.05 |
| Tween 20 | 0.1 |
| TOTAL | 100.00 |

| | Example 24 |
|---|---|
| Part A | |
| Glycerine | 2.5 |
| Methyl Paraben | 0.025 |
| Propyl Paraben | 0.025 |
| Water | 38.75 |
| Sorbitol 70% sol'n | 6 |
| Sodium Saccharin | 0.2 |
| Magnesium Chloride | 0.75 |
| Calcium Lactate Pentahydrate | 1.25 |
| Flavor | 0.4 |
| Tween 20 | 0.1 |
| Part B | |
| Glycerine | 5 |
| Water | 34.825 |
| Sorbitol 70% sol'n | 7.5 |
| Sodium Fluoride | 0.05 |
| Sodium Saccharin | 0.125 |
| Monoammonium Phosphate | 2.25 |
| Flavor | 0.05 |
| Tween 20 | 0.1 |
| Sodium Lauryl Sulfate | 0.1 |
| TOTAL | 100.00 |

EXAMPLES 25–27

Examples 25–27 illustrate professional gel products within the scope of the present invention. The formulations of these products are set forth in Table XII.

TABLE XII

Examples 25–27: Formulations

| | Example 25 |
|---|---|
| Part A | |
| Glycerine | 6.5 |
| Methyl Paraben | 0.025 |
| Propyl Paraben | 0.025 |
| CMC | 0.25 |
| Xanthan Gum | 0.5 |
| Water | 29.95 |
| Sorbitol 70% sol'n | 10 |
| Sodium Saccharin | 0.3 |
| Magnesium Chloride | 0.5 |
| Calcium Lactate Pentahydrate | 0.95 |
| Flavor | 0.5 |
| Tween 20 | 0.5 |
| Part B | |
| Glycerine | 12.5 |
| CMC | 0.25 |
| Xanthan Gum | 0.5 |
| Water | 20.8 |
| Sorbitol 70% sol'n | 10 |
| Sodium Fluoride | 2.5 |
| Sodium Saccharin | 0.3 |
| Monoammonium Phosphate | 2.45 |
| Flavor | 0.35 |
| Tween 20 | 0.35 |
| TOTAL | 100.00 |
| | Example 26 |
| Part A | |
| Glycerine | 10 |
| Methyl Paraben | 0.025 |
| Propyl Paraben | 0.025 |
| CMC | 0.25 |
| Xanthan Gum | 0.5 |
| Water | 30.45 |
| Sorbitol 70% sol'n | 6.5 |
| Sodium Saccharin | 0.3 |
| Magnesium Chloride | 0.6 |
| Calcium Acetate Monohydrate | 0.55 |
| Flavor | 0.4 |
| Tween 20 | 0.4 |
| Part B | |
| Glycerine | 12.5 |
| CMC | 0.25 |
| Xanthan Gum | 0.5 |
| Water | 24.5 |
| Sorbitol 70% sol'n | 5 |
| Sodium Fluoride | 1.25 |
| Sodium Saccharin | 0.3 |
| Monoammonium Phosphate | 5 |
| Flavor | 0.35 |
| Tween 20 | 0.35 |
| TOTAL | 100.00 |
| | Example 27 |
| Part A | |
| Glycerine | 10 |
| Methyl Paraben | 0.025 |
| Propyl Paraben | 0.025 |
| CMC | 0.25 |
| Xanthan Gum | 0.5 |

TABLE XII-continued

Examples 25–27: Formulations

| | |
|---|---|
| Water | 30.45 |
| Sorbitol 70% sol'n | 6.5 |
| Sodium Saccharin | 0.3 |
| Magnesium Chloride | 0.6 |
| Calcium Acetate Monohydrate | 0.55 |
| Flavor | 0.4 |
| Tween 20 | 0.4 |
| Part B | |
| Glycerine | 36.65 |
| Methyl Paraben | 0.025 |
| Propyl Paraben | 0.025 |
| Hydroxypropyl Cellulose | 1 |
| Carbowax 1450 | 2.25 |
| Sodium Fluoride | 1.25 |
| Sodium Saccharin | 0.3 |
| Monoammonium Phosphate | 7.5 |
| Flavor | 0.5 |
| Tween 20 | 0.5 |
| TOTAL | 100.00 |

EXAMPLES 28–31

The formulations of four additional toothpaste products within the scope of the present invention are set forth in Table XIII below. Each of the toothpaste products contains an aqueous portion and a non-aqueous portion as a means for keeping the calcium part from reacting with the phosphate/fluoride part.

TABLE XIII

Examples 28–31: Formulations

| | Example No. Concentration (% wt.) | | | |
|---|---|---|---|---|
| Ingredient | 28 | 29 | 33 | 31 |
| Part A | | | | |
| Calcium Acetate | 1.7 | 0 | 0 | 1 |
| Calcium Gluconate | 0 | 1.5 | 0 | 0 |
| Calcium Nitrate | 0 | 0 | 1 | 0 |
| Magnesium Chloride | 0.5 | 0.8 | 0.4 | 0.4 |
| Pluronic F-127 | 0 | 1 | 2 | 0 |
| Carbowax 8000 | 0 | 0 | 3 | 0 |
| Carbowax E-400 | 0 | 3 | 0 | 0 |
| Water | 37.4 | 0 | 0 | 17.8 |
| Hydrated Silica | 18 | 0.5 | 4 | 8 |
| Glycerine | 10 | 2.6 | 38.47 | 10 |
| Sorbitol | 20 | 0 | 0 | 10 |
| Xanthan Gum | 0.8 | 0 | 0 | 0.5 |
| Flavor | 1 | 0.1 | 0.5 | 0.5 |
| Sodium Saccharin | 0.8 | 0.1 | 0.5 | 0.5 |
| Tween 20 | 0.8 | 0 | 0 | 1 |
| Sodium Lauryl Sulfate | 0.8 | 0 | 0 | 0 |
| Cellulose Gum | 0.5 | 0 | 0 | 0.2 |
| Titanium Dioxide | 0.2 | 0 | 0 | 0 |
| Methyl Paraben | 0.03 | 0.01 | 0.05 | 0.05 |
| Propyl Paraben | 0.03 | 0.01 | 0.05 | 0.05 |
| Part B | | | | |
| Monoammonium Phosphate | 0 | 2 | 0.5 | 0.5 |
| Monosodium Phosphate | 0 | 0 | 1.5 | 1.5 |
| Monopotassium | 0.8 | 0 | 0 | 0 |

TABLE XIII-continued

Examples 28–31: Formulations

| Ingredient | 28 | 29 | 33 | 31 |
|---|---|---|---|---|
| Phosphate |  |  |  |  |
| Dipotassium Phosphate | 0.2 | 0 | 0 | 0 |
| Sodium Fluoride | 0.24 | 0.24 | 0.24 | 0.24 |
| Water | 0 | 37.74 | 21.1 | 0 |
| Hydrated Silica | 0.5 | 17 | 8 | 8 |
| Carbowax 8000 | 0 | 0 | 0 | 3 |
| Carbowax E-400 | 4.8 |  |  |  |
| Pluronic F-108 | 0.8 | 0 | 0 | 2 |
| Glycerine | 0 | 10 | 5 | 32.52 |
| Sorbitol | 0 | 18 | 10 | 0 |
| Xanthan Gum | 0 | 1 | 0.5 | 0 |
| Flavor | 0.05 | 0.9 | 0.5 | 0.5 |
| Sodium Saccharin | 0.05 | 0.9 | 0.5 | 0.5 |
| Tween 20 | 0 | 1 | 1 | 0 |
| Sodium Lauryl Sulfate | 0 | 1 | 0.75 | 1 |
| Cellulose Gum | 0 | 0.3 | 0.2 | 0 |
| Titanium Dioxide | 0 | 0.2 | 0.2 | 0.2 |
| Methyl Paraben | 0 | 0.05 | 0.02 | 0.02 |
| Propyl Paraben | 0 | 0.05 | 0.02 | 0.02 |
| TOTAL | 100 | 100 | 100 | 100 |

The toothpaste product of Example 28 contains about 93% by weight of the calcium-containing portion and about 7% of the phosphate/fluoride-containing portion. In the Example 28 product, the calcium-containing portion is disposed in the aqueous phase and the phosphate/fluoride-containing portion is provided as non-aqueous stripes. The calcium-containing portion is a paste which is mixed in the conventional manner.

The non-aqueous phase of the Example 28 product is prepared by first melting the Pluronic surfactant and the Carbowax and then dissolving them in warm glycerine. The phosphate, fluoride and saccharin ingredients are then suspended therein, followed by silica. Finally, the flavor is added. The non-aqueous phosphate/fluoride portion is a gel and can contain some colorant.

The toothpaste product of Example 29 contains about 10% by weight of the calcium portion and about 90% by weight of the phosphate/fluoride portion. The calcium portion is provided as non-aqueous gel stripes, while the phosphate/fluoride portion is provided as an aqueous paste. The phosphate/fluoride portion is mixed in the conventional manner.

In the Example 29 product, the non-aqueous phase is prepared by melting the Pluronic surfactant and the Carbowax first, then dissolving them in warm glycerine. The calcium salt, magnesium chloride, saccharin and parabens are then blended in, followed by the silica. Finally, the flavor is added.

The calcium portion will be a gel and can contain colorant. Titanium dioxide (preferably in an amount of about 0.2% by weight) could be added to make this into a paste, if desired. The phosphate/fluoride portion is a paste.

Examples 30 and 31 exemplify products wherein the aqueous and non-aqueous portions are provided in equal amounts. These products could be prepared as multi-striped products or as a two-part paste. Part A of Example 30 is prepared similarly to Part A of Example 29. Part B of Example 31 is prepared similarly to Part B of Example 28.

What is claimed is:

1. A two-part oral product for remineralizing at least one subsurface lesion in a tooth and/or mineralizing at least one exposed dentinal tubule of a tooth, comprising:
   (A) a discrete cationic part comprising an effective amount of at least one water-soluble calcium salt, the calcium salt being disposed in a first pharmaceutically acceptable carrier; and
   (B) a discrete anionic part comprising an effective amount of at least one water-soluble phosphate salt, the phosphate salt being disposed in a second pharmaceutically acceptable carrier;
   wherein one of the first and second pharmaceutically acceptable carriers is an aqueous carrier and the other of the carriers is a non-aqueous, hydrophilic carrier.

2. A product according to claim 1, wherein said non-aqueous, hydrophilic carrier is selected from the group consisting of ethyl alcohol, glycerine, propylene glycol and a polyethylene oxide having a molecular weight of about 400.

3. A product according to claim 1, wherein said non-aqueous, hydrophilic carrier is a polyethylene oxide having a molecular weight of about 400.

4. A product according to claim 1, wherein said discrete cationic part and said discrete anionic part are mixed to form a single stable product in which said cationic part and said anionic part remain as discrete parts.

5. A product according to claim 4, wherein said cationic part is disposed as a first discrete stripe and said anionic part is disposed as a second discrete stripe.

6. A product according to claim 5, wherein one of said first and second stripes has a paste-like consistency and the other of said first and second stripes has a gel-like consistency.

7. A product according to claim 1, wherein said cationic part comprises from about 0.05% to about 15.0% by weight of said at least one calcium salt, and said anionic part comprises from about 0.05% to about 15.0% by weight of said at least one phosphate salt.

8. A product according to claim 1, wherein said calcium salt is selected from the group consisting of calcium chloride, calcium nitrate, calcium acetate, calcium lactate, calcium gluconate, and mixtures of the foregoing.

9. A product according to claim 1 wherein said phosphate salt is selected from the group consisting of monoammonium phosphate, monosodium phosphate, monopotassium phosphate and dipotassium phosphate.

10. A product according to claim 1, wherein said cationic part further comprises an effective amount of at least one non-toxic, water-soluble salt of a divalent metal other than calcium.

11. A product according to claim 10, wherein said cationic part comprises from about 0.001% to about 2.0% by weight of said divalent metal salt.

12. A product according to claim 10, wherein the divalent metal is selected from the group consisting of magnesium, strontium, tin and zinc.

13. A product according to claim 12, wherein the divalent metal is magnesium.

14. A product according to claim 13, wherein the divalent metal salt is selected from the group consisting of magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate and magnesium tartrate.

15. A product according to claim 1, wherein said anionic part further comprises an effective amount of at least one water-soluble fluoride salt.

16. A product according to claim 15, wherein said anionic part comprises from about 0.02% to about 2.0% by weight of said fluoride salt.

17. A product according to claim 15, wherein said fluoride salt is selected from the group consisting of alkali metal fluorides, ammonium fluorides and monofluorophosphates.

18. A product according to claim 15, wherein said fluoride salt is sodium fluoride.

19. A product according to claim 1, wherein the product is selected from the group consisting of a toothpaste, a gel, and a professional gel.

20. A product according to claim 1, further wherein the cationic and anionic parts each have a pH in water such that a mixed aqueous solution formed by mixing the parts with water and/or saliva has a pH of from about 4.5 to about 10.0.

21. A method of remineralizing at least one subsurface lesion in a tooth and/or mineralizing at least one exposed dentinal tubule in a tooth, involving the steps of:
 (i) providing a two-part oral product comprising:
  (A) a discrete cationic part comprising an effective amount of at least one water-soluble calcium salt, the calcium salt being disposed in a first pharmaceutically acceptable carrier; and
  (B) a discrete anionic part comprising an effective amount of at least one water-soluble phosphate salt, the phosphate salt being disposed in a second pharmaceutically acceptable carrier;
 wherein one of the first and second pharmaceutically acceptable carriers is an aqueous carrier and the other of the carriers is a non-aqueous, hydrophilic carrier;
 further wherein the cationic and anionic parts each have a pH in water such that a mixed aqueous solution formed by mixing the parts with water and/or saliva has a pH of from about 4.5 to about 10.0; and
 further wherein the cationic and anionic parts are capable of being simultaneously released from the product when the product is mixed with water and/or saliva to form the mixed aqueous solution, such solution containing calcium ions released by the calcium salt and phosphate ions released by the phosphate salt;
 (ii) forming the mixed aqueous solution from the oral product provided in step (i); and
 (iii) applying the mixed aqueous solution to the surface of the tooth promptly after formation of the solution in step (ii), the solution being applied to the surface of the tooth for a period of time sufficient to allow a remineralizing concentration of the dissolved calcium ions and a remineralizing concentration of the dissolved phosphate ions to diffuse through the tooth surface to a subsurface of the tooth, wherein at the subsurface the diffused calcium ions and the diffused phosphate ions react together to form an insoluble precipitate onto the subsurface lesion and/or the exposed dentinal tubule, thereby remineralizing the lesion and/or mineralizing the exposed tubule.

* * * * *